United States Patent [19]
Michelson

[11] Patent Number: 5,613,501
[45] Date of Patent: Mar. 25, 1997

[54] SURGICAL FACE SUPPORT

[75] Inventor: Gary K. Michelson, 438 Sherman Canal, Venice, Calif. 90291

[73] Assignee: Gary K. Michelson, Venice, Calif.

[21] Appl. No.: 75,174

[22] Filed: Jun. 10, 1993

[51] Int. Cl.$^6$ ..................................................... A61F 5/37
[52] U.S. Cl. .................................. 128/846; 5/637; 5/638; 5/639
[58] Field of Search .................................. 128/845, 846, 128/870, 877, 878, 879; 5/636, 637, 640, 644

[56] References Cited

U.S. PATENT DOCUMENTS

| | | | |
|---|---|---|---|
| 1,973,240 | 9/1934 | Werness | 5/636 |
| 2,688,142 | 9/1954 | Jensen | 5/644 |
| 2,795,838 | 6/1957 | McNeely | 5/636 |
| 2,940,087 | 6/1960 | Kiefer | 5/636 |
| 3,482,571 | 12/1969 | Behrendt | 5/637 |
| 4,259,757 | 4/1981 | Watson | 5/637 |
| 4,752,064 | 6/1988 | Voss | 5/636 |
| 5,269,035 | 12/1993 | Hartunian | 5/637 |

*Primary Examiner*—Michael A. Brown
*Attorney, Agent, or Firm*—Lewis Anten, Esq.; Amedeo Ferraro, Esq.

[57] ABSTRACT

The present invention provides a face support device specifically for the purpose of facilitating surgery on humans in the prone position providing for the complete relief of pressure to the areas of the eyes, ears, nose, and mouth of a patient. The face support has a concave curved upper portion, a concave lower surface and a central opening for avoiding pressure on the eyes, nose and lips of the patient, while providing for increased support with decreased pressure and skin shear experienced by the patient's face in contact with the face support.

11 Claims, 4 Drawing Sheets

SURGICAL FACE SUPPORT

BACKGROUND OF THE INVENTION

1. Field of the Invention

The present invention relates to head and face supports used in surgery, and more specifically to head and face supports in which a patient's face rests on the support when the patient is in a prone position as on a spinal surgery support frame.

2. Description of the Related Art

In the past, various devices have been commonly used to support a person's head in the face down position. These support devices were typically made from foams of varying density, some hard, some soft and some a combination of both. Specialized versions of face support devices are commonly used in surgery. One such prior art device is shown in FIG. 1 of the drawings.

The better versions of such devices provided areas of cut-out or relief in and about the region of the eyes to obviate contact with the support and to thereby avoid almost certain damage. A further taking away of material is required to accommodate the prominence of the nose, which would otherwise subject it to extreme pressure. Finally, a still further removal of supporting material is required to accommodate the entire area about the mouth to avoid the lips being injured by direct pressure by the support against the teeth.

The problem, therefore, with all prior art is that in relieving so much relative area of the face from contact with support, there is relatively little residual area of the face left to contact the support device, and to support thereby, the weight of the face and head. Attempts have been made to increase the support area of the device through contouring and to thereby engage the more laterally disposed curved portions of the face. Unfortunately, this has not proven completely effective. Inasmuch as the sides of the head and face are oriented relatively vertical with the patient's face down, attempting to support the face by merely contouring the contact surfaces laterally creates shearing forces between the device and the skin of the sides of the face, a condition which the skin finds particularly injurious.

SUMMARY OF THE PRESENT INVENTION

The present invention provides a face support device specifically for the purpose of facilitating surgery on humans in the prone position providing for the complete relief of pressure to the areas of the eyes, ears, nose, and mouth of a patient. The face support has a concave curved upper portion, a concave lower surface and a central opening for avoiding pressure on the eyes, nose and lips of the patient, while providing for increased support with decreased pressure and skin shear experienced by the patient's face in contact with the face support.

The present invention provides for the improved relief of contact with the surgical face support about the eyes, nose, and lips, and yet provides for an increased area of engagement and support for the face and head. The present invention also provides for the optimal static support of the head and face by its curvilinear and anatomical contouring. However, unlike the prior art, the present invention provides a means for optimally and dynamically providing support to the non-planar and more vertically inclined surfaces (the sides) of the head and face. By contouring of the bottom of the device in such a way that the weight of the patient's own head is used to progressively deform, not only the foam itself of the supporting material, but its overall shape in such a way that the pressure from the weight of the face descending into the device causes an equal and opposite reaction along a vector that is always perpendicular to the plane of the facial structures being engaged. Further, specific to its purpose as a surgical device, the present invention allows for the unimpeded thoroughfare from either side of the endotracheal tube.

OBJECTS OF THE PRESENT INVENTION

It is an object of the present invention to provide a surgical face support that distributes pressure more evenly across the patient's face.

It is another object of the present invention to provide a surgical face support that supports the non-planar surfaces of the patient's face.

It is still another object of the present invention to provide a surgical face support that dynamically distorts its shape as it is used.

It is yet another object of the present invention to provide a surgical face support that provides support proportional to the load applied.

These and other objects and advantages of the present invention will be apparent from a review of the following specification and accompanying drawings.

DESCRIPTION OF THE PREFERRED EMBODIMENT(S)

Figure 1:
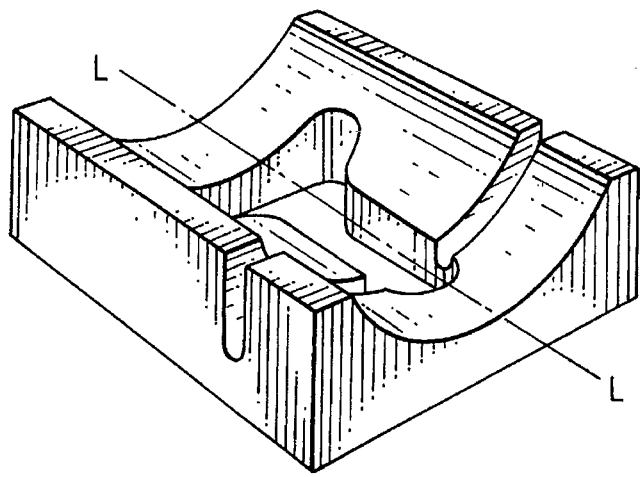
FIG. 1 shows a left perspective view of a face support previously known in the art including center line L—L.

FIG. 1 shows a prior art foam face support device. The support has a central opening to avoid contact with the eyes, nose and lips of the patient. Side slots are also provided for the passage of an endotracheal tube. The bottom surface of the prior art face support is flat. The sides of the upper surface are sloped inwardly. While the patient's head is kept stable by the face support shown in FIG. 1, there is uneven distribution of pressure upon the portions of the patient's face in contact with the support which can lead to pressure related injury during extended surgery. Moreover, the foam of the prior art support compresses in proportion to the weight of the head of the patient on the support.

Figure 2:
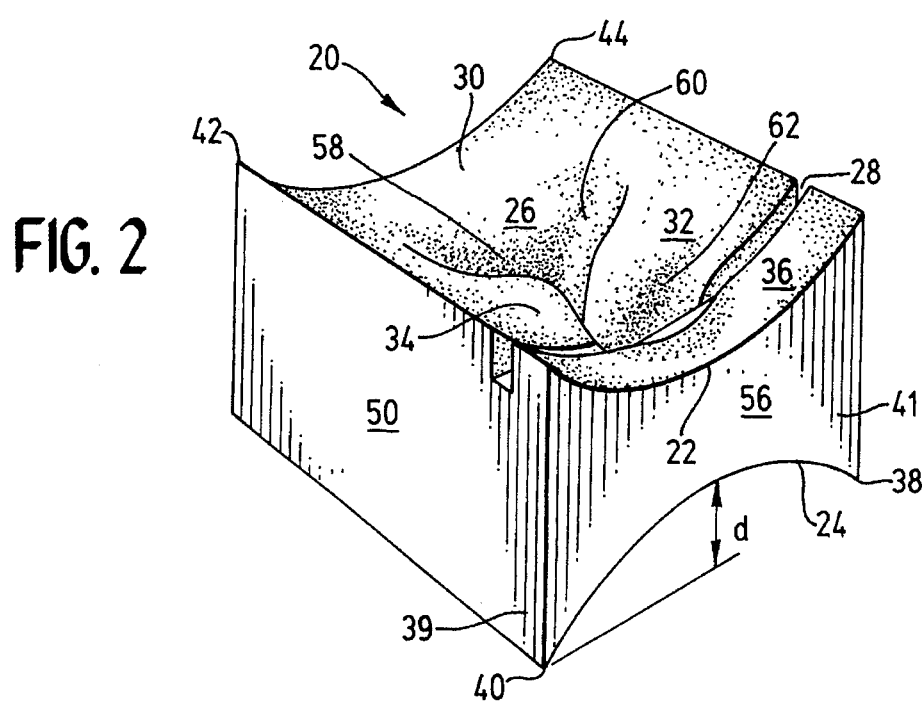
FIG. 2 shows a left perspective view of the face support of the present invention.
Figure 3:
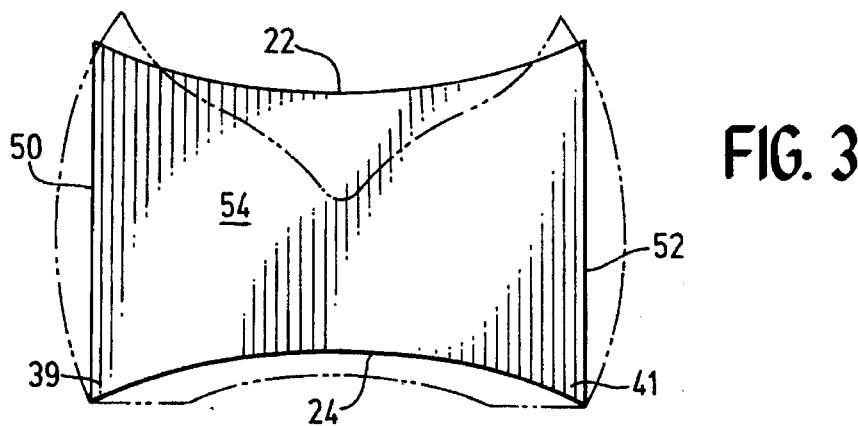
FIG. 3 shows an end view the face support of the present invention.

The face support 20 of the present invention is shown in FIG. 2. In the preferred embodiment, the face support 20 is made from foam and is generally rectangular in shape having side walls 50 and 52, front wall 54 and rear wall 56. The face support 20 has a general concave upper surface 22 and a general concave lower surface 24. The lower concave surface 24 terminates on longitudinal support ends 38 and 40 which form the contact between the face support and the table it rests on. In the preferred embodiment, both concave upper surface 22 and lower concave 24 surfaces are curved along substantially the entire width of the face support 20.

Figure 5:
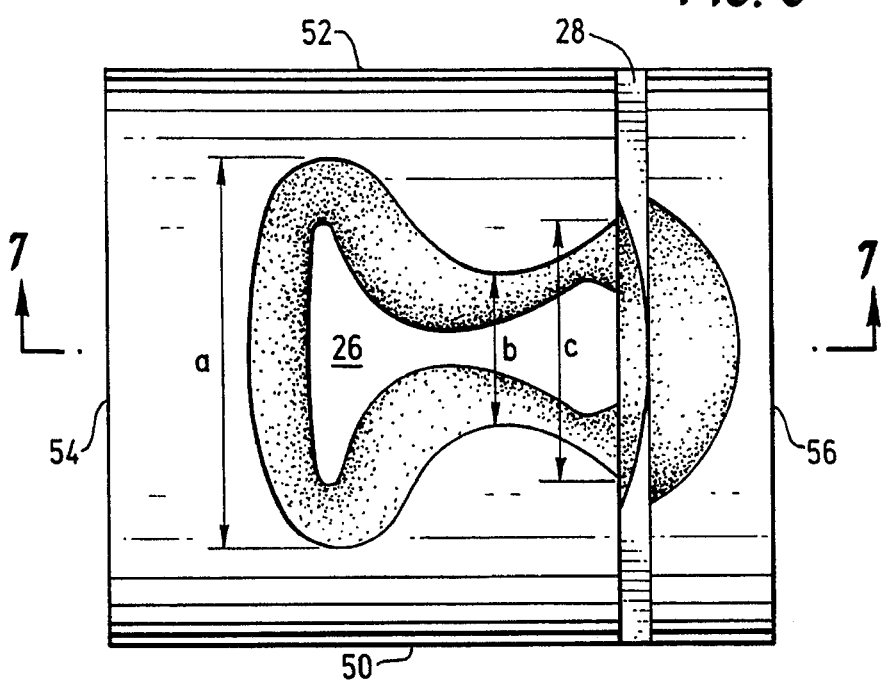
FIG. 5 is a top view of the face support of the present invention.
Figure 6:
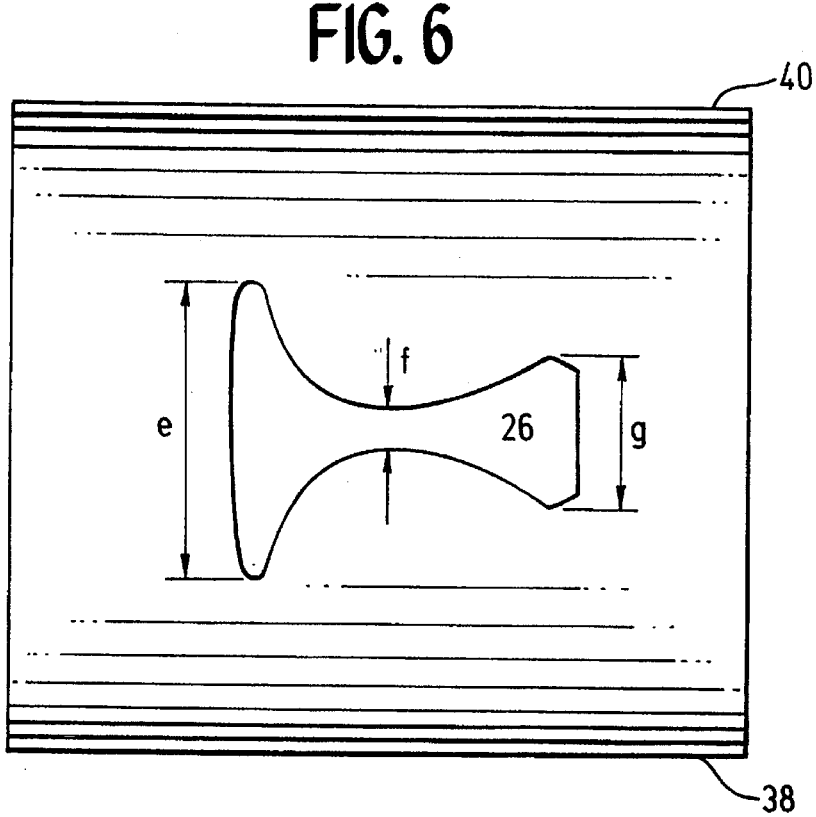
FIG. 6 is a bottom view of the face support of the present invention.
Figure 7:
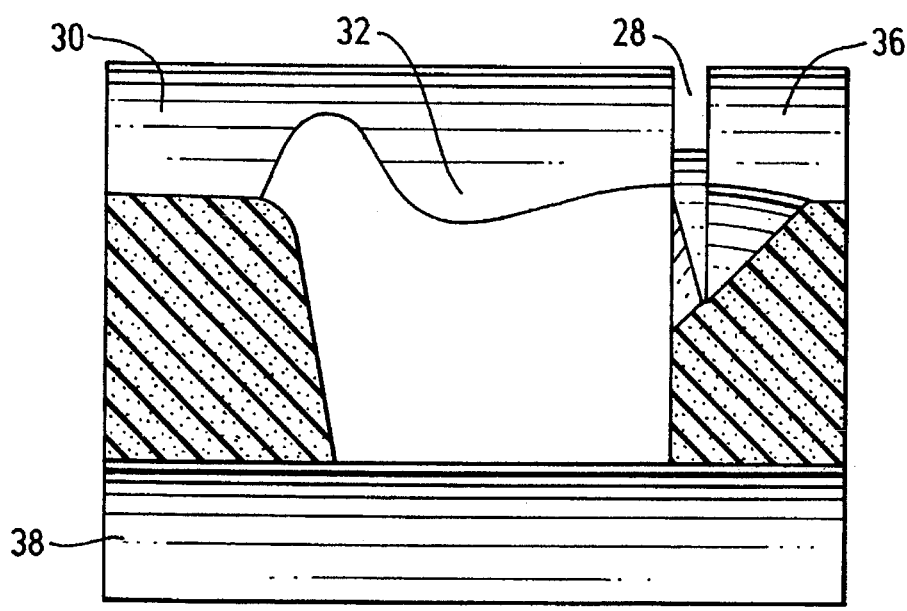
FIG. 7 is a side sectional view taken along lines 7—7 of FIG. 5.

A face opening or aperture 26 is present in the center of the face support 20 and passes through the entire face support. The face opening 26 is wider at its top to accommodate the orbits of the eyes of the patient, narrows at the center to support the cheekbones and accommodate the nose, and widens again at the bottom to accommodate the lips. The walls 58 and 60 of the face opening 26 are sloped gently inwardly so that the face opening 26 narrows from the concave upper surface 22 to the concave lower surface 24, as shown in FIGS. 5 and 6. The face opening 26 is open at the bottom of the face support 20 permitting the progressive recruitment of the foam as load is applied to the face support 20.

A narrow channel 28 spans the width of the concave upper surface 22 of the face support 20 towards the bottom end 62 of the face opening 26. The channel 28 may be of constant depth within the face support 20, or may vary in its depth. The position of the channel 28 corresponds closely to the anticipated location of the mouth of the patient P and permits an endotracheal tube T to be passed to the mouth of the patient P.

Support for the patient's face is provided at several locations by the face support 20. The patient's forehead is supported at the top of the face support 20 by the upper lateral section 30 above the face opening 26. The patient's cheekbone eminences are supported by side lobes 32 and 34 extending into the face opening 26. The patient's chin is supported at the bottom of the face support 20 by the lower lateral section 36. The result is that the bony prominences (brow, cheek, and chin) of the face are supported by the face support 20 of the present invention.

The operation of the face support 20 will now be discussed. When a patient is first anesthetized, he or she is usually laying down face-up. After becoming unconscious, the patient P is rolled over and positioned on a surgical frame in order to perform the required surgery. The patient's face is placed on the concave upper surface 22 of the face support 20 so that the eyes, nose, and mouth are positioned in the face opening 26, but the forehead, cheekbones, and chin of the patient are supported on upper lateral section 30, side lobes 32 and 34 and on lower lateral support 36, respectively. Any required respiratory connections with the patient's mouth such as to endotracheal tubes, can be placed prior to placing the patient's face in the face support 20.

Figure 4:
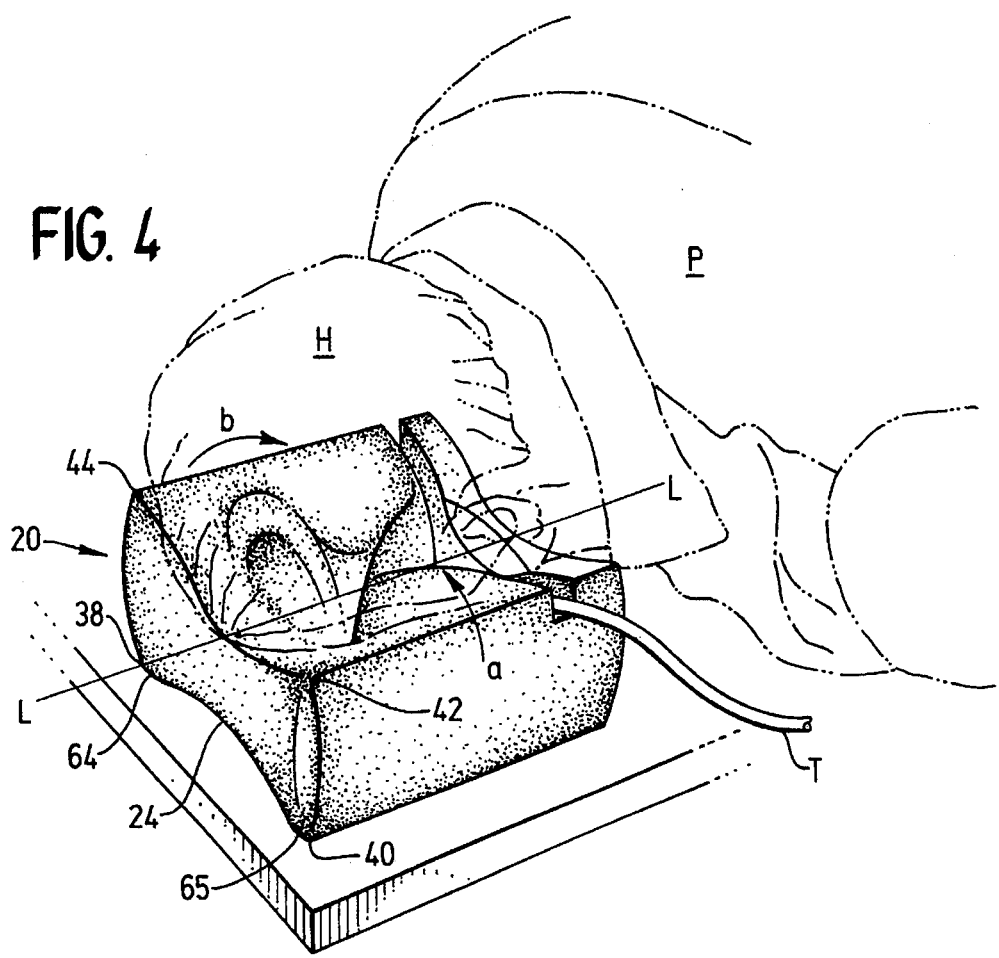
FIG. 4 shows the face support of the present invention in perspective view in partial compression while in use by a patient.

As shown in FIG. 4, when the patient's face is seated against and is supported by the face support 20, the longitudinal support ends 38 and 40 along the sides of the lower concave surface 24 provide the face support 20 with its contact against the operating table or other stable surface. As force is applied by the weight of the patient's head H to the face support 20, center line L—L folds downward and away from the patients head H, while the longitudinal support ends 38 and 40 push up against the patient's face. As the downward force from the patient's head H is applied to the face support 20, the force causes a dynamic deformation of the curvature of the lower concave surface 24, as shown by the flattened portions 64 and 65 in FIG. 4. The downward force of the face also causes the side ends 42 and 44 of the concave upper surface 24 to apply forces that direct the side lobes 32 and 34 and side edges 42 and 44 inwardly towards the center line L—L, as shown in FIG. 4 by arrows a and b, resulting in an evenly distributed force of the side lobes 32 and 34 against the side of the face of the patient. As the downward force of the patient's head H is not opposing the force of the side lobes 32 and 34 of the upper surface 22, the side lobes 32 and 34 tend to wrap themselves around the patient's face and bend in, providing support for the sides of the patient's face, thereby limiting shear forces against the skin of the patient P. Also, this provides a greater distribution of force over a greater contact surface area between the face support 20 and the patient's face.

Also, due to the triangular cross sections 39 and 41, of support ends 38 and 40, as more force is applied downwardly, as in the case with larger and heavy patients, there is increased resistance from the greater cross section of the foam the triangular cross sections 39 and 41.

In the preferred embodiment, the face support 20 is constructed from polyurethane foam material having a density of 1.85 medium. A typical foam rubber face support 20 is approximately 8.0 inches long, 8.0 inches wide, and approximately 6.0 inches tall.

As shown in FIG. 2, the height "d" of the concave lower surface 24 above the line connecting longitudinal support edges 38 and 40 is approximately 1.0 inches. The depth of the concave upper surface 22 is approximately 1.0 inches. The face opening 26 is approximately 6.0 inches from top to bottom.

Referring to FIG. 5, the face opening 26 at the concave upper surface 22 at its upper lateral section 30 proximate the eyes has a width "a" of approximately 5.0 inches, a width "b" of about 1.0 inches proximate the nose and a width "c" of approximately 2.5 inches proximate the chin.

The face opening 26 on the concave lower surface 24 is smaller than the opening in the upper surface, as shown in FIG. 6, thereby increasing the amount of support available from the foam. The face opening 26 in the concave lower surface 24 has a width "e" of approximately 2.5 inches proximate the eyes, a width "f" of approximately 0.175 proximate the nose, and a width "g" of approximately 1.0 inches proximate the chin. The use of the smaller face opening 26 in the concave lower surface 24 results in a sloping contour which permits increased support from the foam in the areas below the portions of the face in contact with the face support.

Figure 8:
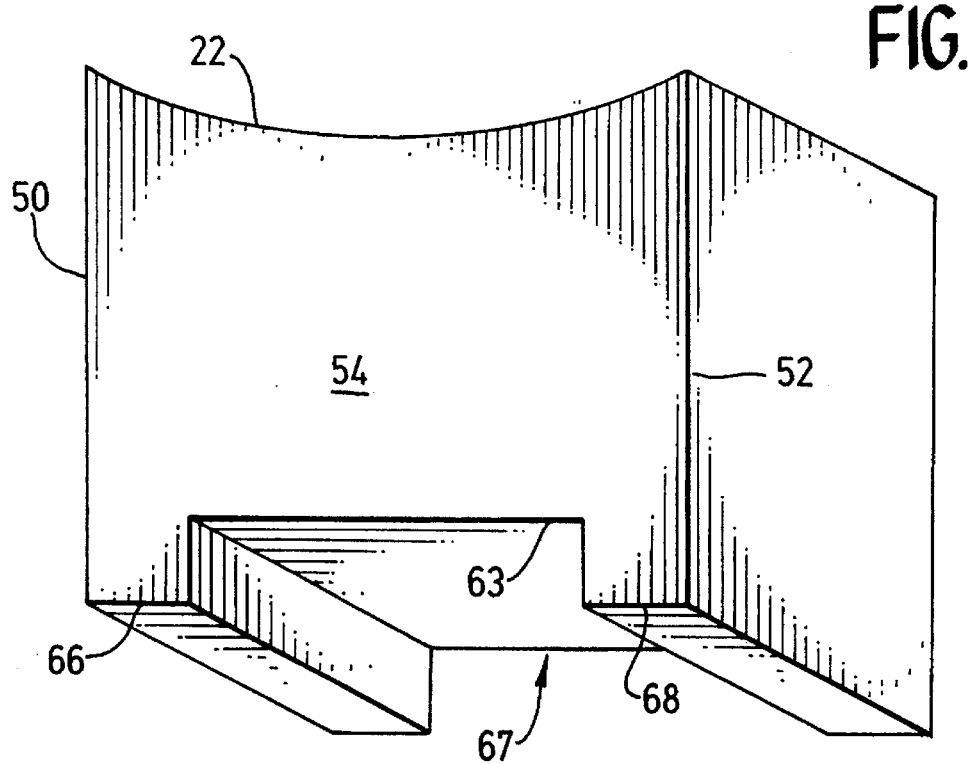
FIG. 8 is a alternative embodiment of the face support of the present invention with blocks to create a raised central portion.

An alternative embodiment of the present invention is shown in FIG. 8 where a straight lower surface 63 is used, instead of a concave curved surface. A raised central portion 67 is created by securing feet 66 and 68 at the side of the straight lower surface 63. In this manner, the straight lower surface 63 is raised from the operating table or other supporting surface, so that the height of the straight lower surface 63 above the line connecting feet 66 and 68 is approximately 1.0 inches.

When the patient's head H is placed on the face support of the alternative embodiment shown in FIG. 8, the weight of the head causes the face support to compress so that the straight lower surface 63 is pushed down and bends outwardly creating the same effect as if the lower surface was curved as in the preferred invention described above.

Feet 66 and 68 may be composed of the same foam material described that is used to make the rest of the face support as discussed above. The feet 66 and 68 may be secured to the bottom of surface 24 by well known adhering means such as glue, welding, or any other means. The feet may also be made from denser material than the rest of the face support. For example, a foam material of a higher density than the foam used for the face support may be used so that the feet are more resistant to the compressive forces exerted upon the face support so that the straight lower surface 63 is compressed before the feet 66 and 68 are compressed.

While the present invention has been described with regards to the preferred embodiments, it is recognized that additional variations of the present invention may be devised without departing from the inventive concept.

Figure 9:
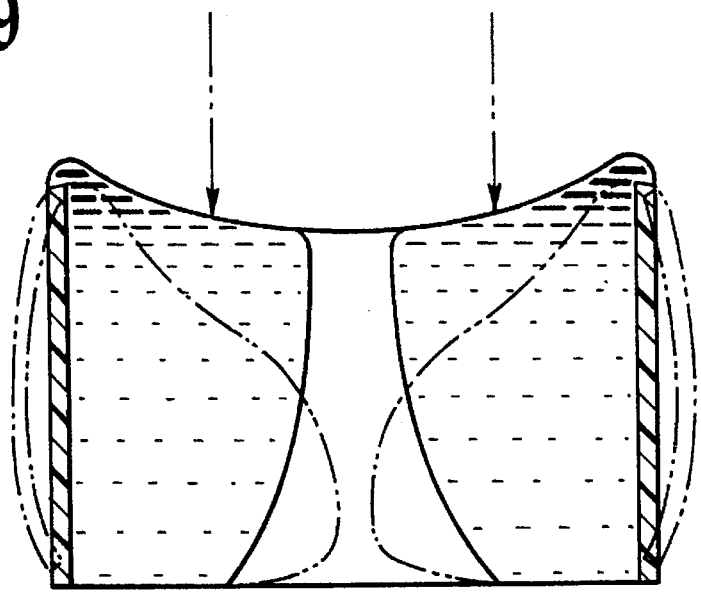
FIG. 9 is another alternative embodiment of the face support of the present invention with a fluid containing bladder and the displacement of the fluid shown in fantom when force is applied to the face support.

For example, the present invention relies on the fact that at least some part of this device is an elastic solid, e.g. foam, and therefore, behaving as an elastic body. However, the result may be achieved by other means. For example, a face support may comprise an appropriately contoured bladder with a relatively incompressible fluid or gel with or without additional padding. The bladder can be made from an elastic material capable of maintaining a preformed shape and resistant to puncturing. The fluid or gel would also allow for the utilization of the weight of the head to displace the internal contents of the face support such that the sides and angles of the faces and parts of the head could be appropriately pressurized and supported, as the pressure would tend to be automatically equalized avoiding high peak contact pressures (law of Laplace). An embodiment of the present invention with a contoured bladder containing a fluid is shown in FIG. 9 with the displacement of the fluid shown in fantom as the force is applied to the bladder.

As a gas has both indefinite volume and shape, by limiting the volume and defining the shape, it is possible to achieve the same end resolved by filling the bladder with an appropriate gas.

What is claimed is:

1. A surgical face support, comprising:

a body made of a compressible material having exterior side walls, end walls, an upper surface for supporting the face of a patient, and a lower surface;

a portion of the upper surface being concave curved in the direction from one side wall to the other side wall;

a portion of the lower surface having a raised central portion; and said upper surface having support means for supporting the sides of a patient's face, said support means comprising an opening for providing space for the patient's eyes, nose, and mouth whereby when a patient's face is seated against said face support a first dynamic downward force from the weight of the patient's head causes said raised central portion to move downward resulting in the deformation of the raised central portion of said lower surface resulting in a second side vector force which causes the lower ends of the side walls to move outwardly so that a third stable force diverts said support means towards the face of the patient, resulting in an evenly distributed force at an angle to said first downward force and against the side of the face of the patient.

2. The face support of claim 1 in which the lower surface is concave curved from one side wall to the other side wall.

3. The face support of claim 1 in which the cross sectional area of the body increases from the upper surface to the lower surface.

4. The face support of claim 1 in which said upper surface includes a channel therein for receiving respiratory connecting means for connection to the patient's mouth.

5. The face support of claim 1 in which said opening has inwardly sloping interior walls for supporting the sides of the patient's face.

6. A surgical face support, comprising a body member made of a compressible material having side walls and end walls, a concavedly curved upper surface being curved from one side wall to the other side wall of said body and a concavedly curved lower surface being curved from one side wall to the other side wall;

said upper surface including facial support means for supporting the face of a patient, said facial support means comprising an opening in said upper surface, said opening providing space for a patient's eyes, nose, and mouth so that the face support does not come into contact with the patient's eyes, nose, and mouth, said opening being larger on its top surface than below the upper surface, and said opening having inwardly sloping interior walls for supporting the sides of the patient's face.

7. A surgical face support for supporting the face of a patient in a prone position on a patient supporting surface, comprising:

a block made of a compressible material having side walls, a concavedly curved upper surface for supporting the face of a patient, a lower surface having a central portion and means for holding said central portion in a raised position relative to the patient supporting surface;

said upper surface having facial support means for supporting the sides of a patient's face, said facial support means comprising an opening providing space for a patient's eyes, nose, and mouth, at least a portion of said central portion being located below said opening in said upper surface.

8. The surgical face support of claim 7 in which said means for holding said central portion in a raised position comprises downwardly projecting feet projecting from said lower surface.

9. The surgical face support of claim 8 in which said feet comprise a pair of support blocks, each of said pair of support blocks being parallel to said side walls and substantially the same width of said side walls.

10. A surgical face support, comprising:

a body made of a compressible material having side exterior walls, and end walls;

a concavedly curved upper surface being curved from one side wall to the other side wall;

a concavedly curved lower surface being curved from one side wall to the other side wall, said lower surface having a raised central portion; and said upper surface including a facial support means for supporting the face of a patent, said facial support means comprising an opening decreasing in size from said top surface toward said bottom surface and having inwardly sloping interior walls for supporting the sides of the patient's face, said opening providing space for a patient's eyes, nose, and mouth, whereby when a patient's face is seated against said face support a first dynamic downward force from the weight of the patient's head causes said raised central portion to move downward resulting in the deformation of the curvature of said lower concave surface resulting in a second side vector force which causes the lower ends of the side walls to move outwardly so that a third stable force diverts inwardly sloping interior walls towards the face of the patient, resulting in an evenly distributed force at an angle to said first downward force and against the side of the face of the patient.

11. A surgical face support, comprising a block having side walls, said side walls having upper and lower ends;

a concavedly curved upper surface;

a flat lower surface;

a plurality of support feet secured to said lower surface so that said lower surface has a raised central portion when said feet are placed on an operating table or other stable surface;

said upper surface including a hole therein, said hole providing space for a patient's eyes, nose, and mouth;

whereby when a patient's face is seated against said face support a first dynamic downward force from the patient's head causes said raised central portion to lower and deform resulting in a second side vector force which causes the lower ends of the side walls to move outwardly so that a third stable force diverts said upper surface inwardly towards the face of the patient, resulting in an evenly distributed force of said upper surface against the side of the face of the patient.

* * * * *